US010849989B2

(12) United States Patent
Hudson et al.

(10) Patent No.: US 10,849,989 B2
(45) Date of Patent: Dec. 1, 2020

(54) ISOLATED COMPOSITE DRUG AND CARRIER NANOPARTICLES

(71) Applicant: University of Limerick, Limerick (IE)

(72) Inventors: Sarah Hudson, Limerick (IE); Teresa Tierney, Limerick (IE); Ake Rasmuson, Limerick (IE); Katalin Bodnar, Limerick (IE)

(73) Assignee: University of Limerick, Plassey (IE)

( * ) Notice: Subject to any disclaimer, the term of this patent is extended or adjusted under 35 U.S.C. 154(b) by 0 days.

(21) Appl. No.: 16/331,296

(22) PCT Filed: Sep. 7, 2017

(86) PCT No.: PCT/EP2017/072450
§ 371 (c)(1),
(2) Date: Mar. 7, 2019

(87) PCT Pub. No.: WO2018/046591
PCT Pub. Date: Mar. 15, 2018

(65) Prior Publication Data
US 2019/0262472 A1 Aug. 29, 2019

(30) Foreign Application Priority Data

Sep. 7, 2016 (GB) .................................. 1615196.1

(51) Int. Cl.
*A61K 47/69* (2017.01)
*A61K 9/14* (2006.01)
(Continued)

(52) U.S. Cl.
CPC .......... *A61K 47/6949* (2017.08); *A61K 9/141* (2013.01); *A61K 9/5192* (2013.01);
(Continued)

(58) Field of Classification Search
CPC ............ A61K 47/6949; A61K 47/6929; A61K 9/5192; A61K 33/06; B92Y 5/00; B82Y 30/00
See application file for complete search history.

(56) References Cited

U.S. PATENT DOCUMENTS

| 2010/0168044 | A1 | 7/2010 | Misra |
| 2011/0269723 | A1 | 11/2011 | Asotra et al. |
| 2012/0183588 | A1* | 7/2012 | Supamahitorn ........ A01N 39/00 424/401 |

FOREIGN PATENT DOCUMENTS

| CN | 103251956 A | 8/2013 |
| EP | 3012225 A1 | 4/2016 |

(Continued)

OTHER PUBLICATIONS

Wang et al, "Mesoporous Silica Nanoparticles in Drug Delivery and Biomedical Applications", Nanomedicine: Nanotechnology, Biology, and Medicine, vol. 11, No. 2, (Year: 2015).*

Yang Wang et al., "Mesoporous silica nanoparticles in drug delivery and biomedical applications", Nanomedicine: Nanotechnology, Biology and Medicine, vol. 11, No. 2, Feb. 1, 2015, pp. 313-327.

(Continued)

*Primary Examiner* — Carlos A Azpuru
(74) *Attorney, Agent, or Firm* — Hamilton, Brook, Smith & Reynolds, P.C.

(57) ABSTRACT

A process for the preparation of a composite comprising a carrier particle and a plurality of drug nanoparticles. The process comprises providing a suspension of drug nanoparticles in the presence of a carrier particle, the carrier particle having an external surface that is functionalised with a surface treatment agent. The process simplifies isolation of drug nanoparticles from suspension.

19 Claims, 6 Drawing Sheets

(51) Int. Cl.
    *A61K 9/51*    (2006.01)
    *A61K 33/06*   (2006.01)
    *B82Y 5/00*    (2011.01)
    *B82Y 30/00*   (2011.01)
(52) U.S. Cl.
    CPC .......... *A61K 33/06* (2013.01); *A61K 47/6929* (2017.08); *B82Y 5/00* (2013.01); *B82Y 30/00* (2013.01)

(56) References Cited

FOREIGN PATENT DOCUMENTS

| KR | 101567717 B | 11/2010 |
|----|-------------|---------|
| WO | 2010063998 A2 | 6/2010 |
| WO | 2015042268 A1 | 3/2015 |
| WO | 2016134115 A1 | 8/2016 |
| WO | 2018046591 | 3/2018 |

OTHER PUBLICATIONS

Zhang Chen et al., "Poly dimethyl diallyl ammonium coated CMK-5 for sustained oral drug release", International Journal of Pharmaceutics, Elsevier, vol. 461, No. 1, Dec. 1, 2013, pp. 171-180.

International Search Report and Written Opinion of the International Searching Authority for International Application No. PCT/EP2017/072450, entitled: "Method for Stabilising and Isolating Nanoparticles,", dated Jul. 12, 2017.

Piludi, et al., "Silver Enhancement for Transmission Electron Microscopy Imaging of Antibody Fragment-Gold Nanoparticles Conjugates Immobilized on Ordered Mesoporous Silica", American Chemical Society, Langmuir, 2015, 31, pp. 9458-9463.

Liu, et al., "PEGylated FePt@Fe2O3 core-shell magnetic Nanoparticles: Potential theranostic applications and in vivo toxicity studies", Nanomedicine: NBM 2013;9:1077-1088.

Mo, et al., "Dual-Functionalized Theranostic Nanocarriers", ACS Applied Materials & Interfaces, 2016, 8, 14740-14746.

GB Search Report for Application No. GB1615196.1 dated May 9, 2017.

\* cited by examiner

ISOLATED COMPOSITE DRUG AND CARRIER NANOPARTICLES

This application is the U.S. National Stage of International Application No. PCT/EP2017/072450, filed Sep. 7, 2017, which designates the U.S., published in English, and claims priority under 35 U.S.C. § 119 or 365(c) to GB Application No. 1615196.1, filed Sep. 7, 2016.

This invention relates to carrier-nanoparticle composites useful for stabilising and isolating drug nanoparticles from suspension, and a method for their preparation.

BACKGROUND OF THE INVENTION

Many potential active pharmaceutical ingredient (API) candidates have poor water solubility and slow dissolution rates in vivo, leading to limited bioavailability and failure to reach the market. The production of nanoparticles of poorly water soluble drugs is an accepted method of improving dissolution rates. Current manufacturing practice uses disintegration techniques (i.e. top-down comminution) such as grinding to produce such nanoparticles. This however requires large amounts of energy, is not suitable for heat sensitive drugs and exhibits limited control over crystallinity and final crystal form. A "bottom-up" approach uses supersaturated solutions to generate high nucleation rates and thus can nucleate many particles simultaneously while controlling the polymorphic form. The size of these particles can initially be in the nanometre range but they quickly grow (by aggregation or Ostwald ripening) to larger particles. To avoid particle growth and the loss of the high surface area of the nanoparticles, stabilisation and/or fast isolation is required. This has proven challenging and difficult to scale up.

For long term stabilisation and for convenience during oral administration, nanoparticles are often isolated in the solid state for incorporation into solid dosage forms such as tablets. Conventional nanoparticle isolation techniques (e.g. freeze-drying, spray-drying and centrifugation) are quite complex processes which can induce nanoparticle aggregation and consequential reduction in dissolution rate compared to suspended nanoparticles. Some alternative nanoparticle isolation strategies have been proposed in recent years, e.g. nanoparticle coating onto water-soluble carriers in a fluidised bed, reversible salt-flocculation and filtration, and matrix formers for aggregation prevention during spray drying. Khan et al. (S. Khan, M. de Matas, S. Plakkot and J. Anwar, Cryst. Growth Des., 2014, 14, 1003-1009) presented an application for carrier-mediated isolation of drug nanocrystals from suspension, in which insoluble dibasic calcium phosphate carrier particles captured nanocrystals of ibuprofen and glibenclamide from suspension and the composites were isolated by filtration. However, the process was limited by a low maximum drug loading of 0.35%, restricting its application to high potency drugs. In addition, prior knowledge of drug-specific, soluble stabilisers was required.

Piludu et al (Langmuir, 2015, 31, 9458-9463, ISSN 1520-5827) describes a method for carrying out transition electron microscopy imaging of an antibody. The antibody is covalently bonded to a gold nanoparticle (GNP) to form a conjugate, and the conjugate is immobilised on ordered mesoporous silica (OMS). No drug nanoparticles are present.

Liu et al (Nanomedicine; nanotechnology, biology and medicine, 2013, (9), 1077-1088, ISSN 1549-9642) describe a core-shell magnetic nanoparticle as a magnetic resonance (MR) imaging contrast agent and as a carrier for doxorubicin molecules. No drug nanoparticles are present; the doxorubicin molecules are loaded onto the nanoparticle from solution.

Mo et al (ACS Appl. Mater. Interfaces, 2016, 8, 14740-14746, ISSN 1944-8252) describes the capture of gold nanoparticles on silica nanocarriers. No drug nanoparticles are present.

US 2010/0168044 describes a super paramagnetic nanoparticle encapsulated with stimuli responsive polymer for drug delivery. No drug nanoparticles are present; drug molecules are loaded onto the nanoparticle from solution and subsequently encapsulated in polymer.

WO 2016/134115 describes a microbubble with a Janus nanoparticle associated with the surface. The Janus nanoparticle has a nucleic acid delivery face and a targeting face. No drug nanoparticles are present; nucleic acid molecules may be adsorbed onto the nucleic acid delivery face.

EP 3012225 describes a disinfectant containing a titanium oxide nanomaterial to which herbal and fruit extracts are adsorbed. No drug nanoparticles are present; the extracts are adsorbed onto the nanomaterial from aqueous solution.

CN 103251956 A describes the use of a montmorillonite-matrine composite for slow release drug delivery. Matrine molecules are adsorbed to the montmorillonite from solution; no drug nanoparticles are present.

KR 101567717 B describes a nanocomplex for treating cancer. The nanocomplex comprises a nanoparticle (formed from calcium ions and an anionic hydrophilic photosensitizer) that is coated with a branched polyethyleneimine or protamine sulphate.

SUMMARY OF THE INVENTION

According to a first aspect of the present invention there is provided a composite comprising a carrier particle and a plurality of drug nanoparticles, wherein the carrier particle has an external surface that is functionalised with a surface treatment agent and the plurality of drug nanoparticles is adsorbed onto the functionalised external surface.

The composites of the invention are more stable in suspension than "free" drug nanoparticles. In addition, they are easier to separate from solution and simple filtration is possible. The drug nanoparticle composites maintain the fast dissolution rate of corresponding "free" nano-particles and are therefore expected to exhibit good dissolution behaviour in vivo, leading to high bioavailability.

It will be understood that the surface treatment agent modifies the properties of the external surface of the carrier particle. For example, the surface treatment agent may make regions of the surface more hydrophobic or more hydrophilic. The surface treatment agent may increase or decrease the electrostatic charge at the surface of the carrier particle. Without being bound by theory, the inventors propose that the amount and distribution of the surface treatment agent affects the amount and distribution of the drug nanoparticles which attach.

The zeta potential is an important concept for particles in suspension. Zeta potential is a measure of the magnitude of the electrostatic repulsion/attraction between particles. Zeta potential can be considered to be the potential difference between the dispersion medium and the stationary layer of fluid attached to the dispersed (suspended) particle. Low magnitude zeta potential values are associated with a low degree of electrostatic repulsion and therefore a tendency for the particles to aggregate. High magnitude zeta potential values are associated with a high degree of electrostatic repulsion between adjacent, similarly charged particles, and hence confers stability.

Zeta potential can be determined from electrophoretic mobility using the Smoluchowski calculation. The electrophoretic mobility value can be determined at 25° C. by electrophoretic light scattering (ELS), e.g. using a Malvern Zetasizer Nano ZSP system. Such commercially available ELS instrumentation will directly provide zeta potential values. Aqueous suspensions are filled into a folded capillary cell and equilibrated at 25° C. for 120 seconds before measurement. Three measurements are taken per run and each sample is run twice. The average value and the variation between measurements can be reported.

Unless otherwise stated, reference to zeta potential is a reference to the zeta potential of a suspension of the particles in water at neutral pH (pH 7) at standard ambient temperature and pressure (SATP, 25° C. and 100 kPa).

The isoelectric point (pI or pH(I)) is another useful concept for understanding the invention. The isoelectric point is the pH (at SATP) at which a particular molecule carries no net electrical charge or has a zeta potential of zero. At a pH above its isoelectric point a molecule carries a net negative charge, or has a negative zeta potential, and at a pH below its isoelectric point a molecule carries a net positive charge or has a positive zeta potential.

The isoelectric point can be determined by measuring zeta potential (at SATP) over a range of pH values.

Carrier Particle(s)

It will be understood that it may not be possible to measure the properties of a single carrier particle, hence the comments below relate to a plurality of such particles where appropriate. In embodiments, a plurality of carrier particles refers to 10 or more, 1000 or more, 100000 or more, or 1000000 or more particles. In embodiments, a plurality of carrier particles refers to at least 1 mg, at least 10 mg or at least 100 mg carrier particles.

In embodiments the carrier particle is water insoluble. A water-insoluble carrier particle provides a useful means for preparing the composite. For example, a water-insoluble carrier particle will be suspended in water or water/solvent mixtures and therefore provide a surface to which the poorly water-soluble drug can adsorb. Water solubility can be defined by reference to the mass that dissolves in 100 ml water at 20° C. and 100 kPa. In embodiments the carrier particle has a solubility of no more than 2.0 g, no more than 1.0 g, no more than 0.20 g, no more than 0.10 g, no more than 0.05 g, or no more than 0.01 g/100 ml, at 20° C. and 100 kPa.

In embodiments the carrier particle is insoluble in an organic solvent, such as ethanol, methanol, acetonitrile, chloroform, diethyl ether or any solvent where a high level of supersaturation of the drug can be obtained. Solubility in a given solvent system can be defined by reference to the mass that dissolves in 100 ml of that solvent system at 20° C. and 100 kPa. In embodiments the carrier particle has a solubility in an organic solvent, such as those mentioned, of no more than 2.0 g, no more than 1.0 g, nor more than 0.20 g, no more than 0.10 g, no more than 0.05 g, or no more than 0.01 g/100 ml, at 20° C. and 100 kPa.

In embodiments the carrier particle has an average particle size ($D_{50}$) of at least 1, 5, 10, 15, 20, 25 or 30 μm and/or no more than 500, 300, 100 or 50 μm. It may not be possible to measure the size (diameter, D) of a specific carrier particle so the size is best described with reference to the average diameter ($D_{50}$) of a plurality of such particles. The use of a relatively large carrier particle allows a simple filtration method to be employed. In one embodiment the carrier particle has an average particle size (median diameter, $D_{50}$) of from 25 to 30 μm.

In embodiments the carrier particle has an average particle size ($D_{50}$) of from 1 to 500 μm, from 5 to 300 μm, from 10 to 100 μm or from 15 to 50 μm. The MMT clay described in the examples has a particle size $D_{50}$ of 28±1.3 μm.

Particle size can be determined by laser diffraction, for example using a Malvern Mastersizer 3000.

It will be understood that the carrier particle must be pharmaceutically acceptable since it is to be employed with drug nanoparticles. In embodiments the carrier particle is an organic carrier particle. Suitable carrier particles may be selected from the group comprising polymers such as microcrystalline cellulose, ethylcellulose, methyl methacrylate, ethyl acrylate, acrylamides, carboxymethyl cellulose, dextran, polycaprolactone, polyvinyl pyrrolidone, polyphosphates, etc.

In one embodiment the carrier particle is an organic carrier particle selected from microcrystalline cellulose, ethylcellulose, methyl methacrylate, ethyl acrylate, acrylamide, polycaprolactone, polyvinyl pyrrolidone, or polyphosphates.

In embodiments the carrier particle is an ethyl acrylate particle. In one such embodiment the ethyl acrylate particle has a particle size of 5 to 300 μm.

In embodiments the carrier particle is an inorganic carrier particle. Suitable inorganic carrier particles may be selected from the group comprising one or more of group I salts and/or oxides, group II salts and/or oxides, transition metal oxides, ceramics (including clay), and silicas.

In one embodiment the carrier particle is selected from group I salts and/or oxides, group II salts and/or oxides, transition metal oxides, ceramics, silicates and silicas.

In embodiments the carrier particle is a silica or a silicate.

In embodiments the carrier particle is a silicate such as a mesoporous silicate (MPS). It is known in the art that MPS can be chemically modified with various functional groups and MPS has been functionalised with (3-aminopropyl) trimethoxysilane (Hudson et al. Chem. Mater. 2007, 19, 2049-2055). This functionalised MPS described in the art is proposed as a support for chloroperoxidase (CPO) enzyme. The enzyme is thought to enter the pores in the MPS and the pore size is 20 nm or less. The MPS has an average zeta potential before functionalisation of −10 to −20 mV and an average zeta potential after functionalisation of 2 to 40 mV.

In embodiments the carrier particle is a clay particle, such as an aluminosilicate clay.

In embodiments the clay particle is a kaolin clay, an illite clay or a smectite clay (e.g. montmorillonite clay).

In embodiments the clay particle is selected from one or more of halloysite, kaolinite, illite, vermiculite, talc, sepiolite, palygorskite, or pyrophyllite.

In one such embodiment the carrier particle is a montmorillonite clay (MMT). MMT is a negatively charged aluminosilicate clay with high ion-exchange capacity. Aluminosilicate clay has FDA approval as an inactive ingredient.

The surface of montmorillonite clay contains segregated regions of hydrophobicity and charge-induced hydrophilicity. Siloxane (≡Si—O—Si≡) units cover much of its exposed surface, giving the material a hydrophobic nature due to strong bonding interactions between silicon and oxygen atoms. However, isomorphous substitution of surface atoms (e.g. $Si^{4+}$ by $Al^{3+}$) provides diffuse regions of (hydrophilic) negative charge across its surface. Negative charges are balanced by adsorption of loosely-bound exchangeable inorganic counterions (e.g. $Na^+$, $K^+$), giving the material high ion exchange capacity for cations such as protamine. The surface properties of the clay greatly affect the affinity and thus the binding potential and binding mechanism of drug nanoparticles.

In embodiments the carrier particle (without surface functionalisation) has a zeta potential of from −100 mV to +100 mV, from −50 mV to +50 mV or from −30 mV to +30 mV (suspension in water at pH 7, SATP).

In embodiments the carrier particle (without surface functionalisation) has a zeta potential of less than zero i.e. it is negatively charged.

In embodiments the carrier particle has a zeta potential of less than −1, −3, −5, −7, −10, −15, −20, −25, −30 or −35 mV and/or at least −100, −80, −60, −40 −30 or −20 mV.

In embodiments the carrier particle (without surface functionalisation) has a zeta potential of from −100 mV to −1 mV, from −60 to −5 mV or from −30 to −10 mV. The MMT exemplified in the present application has an average zeta potential of −26.9±3.0 mV before functionalisation.

In embodiments the carrier particle has a zeta potential of greater than zero i.e. it is positively charged.

In embodiments the carrier particle (without surface functionalisation) has a zeta potential of at least 1, 3, 5, 7, 10, 15, 20, 25, 30 or 35 mV and/or at no more than 100, 80, 60, 40, 30 or 20 mV.

In embodiments the carrier particle (without surface functionalisation) has a zeta potential of from 1 to 100 mV, from 5 to 60 mV, from 10 to 30 mV.

Surface Treatment Agent

The surface treatment agent functionalises the external surface of the carrier particle. The surface treatment agent can be considered to bond to the external surface of the carrier particle, by physical or chemical bonding.

In embodiments the surface treatment agent is physically bonded to the surface, e.g. the surface treatment agent may adsorb to the surface by Van der Waals forces, hydrogen bonding, ion exchange etc.

In embodiments the surface treatment agent adsorbs to the surface of the carrier particle, for example by means of an ion-exchange process. In which case the surface treatment agent is not permanently bonded to the carrier particle.

In embodiments the surface treatment agent is chemically bonded to the surface, e.g. the surface treatment agent may be covalently bonded to the surface.

The zeta potential of the carrier particle can be measured with and without the surface treatment agent to determine the effect of degree of functionalisation on zeta potential.

In embodiments where the carrier particle has a negative zeta potential, functionalisation with the surface treatment agent may reduce the negative value, i.e. make the carrier particle more positive. In a series of embodiments functionalisation with the surface treatment agent reduces the negative zeta potential of the carrier particle by at least 5, 10, 15 or 20 mV relative to the carrier particle without surface treatment agent. In embodiments functionalisation with the surface treatment agent reduces the negative zeta potential of the carrier particle by no more than 30, 25, 20 or 15 mV relative to the carrier particle without functionalisation. In one embodiment functionalisation with the surface treatment agent reduces the negative zeta potential of the carrier particle by 15 to 30 mV.

The examples of the present invention demonstrate that MMT clay has a zeta potential of −26.9 mV without protamine, −6 mV when sparsely functionalised with protamine and +14.8 mV when saturated with protamine. Hence, the addition of protamine reduces the magnitude of the negative zeta potential of MMT. As demonstrated in the examples, a reduction in zeta potential of MMT increases the drug loading whilst maintaining stability of suspension.

In embodiments where the carrier particle has a positive zeta potential, functionalisation may reduce the positive value, i.e. make the carrier particle more negative. In a series of embodiments functionalisation reduces the positive zeta potential of the carrier particle by at least 5, 10, 15 or 20 mV relative to the carrier particle without the surface treatment agent. In embodiments functionalisation reduces the positive zeta potential of the carrier particle by no more than 30, 25, 20 or 15 mV relative to the carrier particle without the surface treatment agent. In one embodiment functionalisation reduces the positive zeta potential of the carrier particle by 15 to 30 mV.

In embodiments functionalisation increases the magnitude of the zeta potential of the carrier particle (whether positive or negative). In embodiments functionalisation increases the magnitude of the zeta potential by at least 5, 10 or 15 mV relative to the carrier particle without surface treatment agent.

In embodiments the surface treatment agent is water-soluble.

In embodiments the surface treatment agent is charged in water at neutral pH i.e. a positively charged surface treatment agent or a negatively charged surface treatment agent. A charged surface treatment agent may adsorb to the carrier material by means of an ion-exchange process.

The surface treatment agent may be described with reference to its $pK_a$ value(s). $pK_a = -\log_{10}K_a$ and $K_a$ is the acid dissociation constant. The larger the value of $pK_a$, the smaller the extent of dissociation at any given pH and thus the less charge present.

$pK_a$ values can be measured for some materials by potentiometric titration and spectrophotometric titration methods and these methods are outlined in the Organisation for Economic Co-operation and Development (OECD) Guideline 112 and are also described in Albert, A.; Serjeant, E. P., The Determination of Ionisation constants. Chapman and Hall, London, 2nd Edition 1984. Such samples are required to be electrically conduct or have appreciably different UV/VIS-absorption spectra for the dissociated and undissociated forms.

The $pK_a$ value is most useful when a surface treatment agent has a single group that can become charged. In such embodiments a pKa value less than 7 means that the molecule will have a negative charge in at neutral pH (pH 7) and a pKa value greater than 7 means that the molecule will have a positive charge at neutral pH.

Many molecules have more than one group that can become charged and therefore more than one pKa value. In such cases the isoelectric point (pI) can be a more useful parameter. For example, an amino acid having one amino group and one carbonyl group will have a pKa value for each group. The isoelectric point of an amino acid is the mean of the two pKa values.

The table below provides examples of suitable surface treatment agents and an indication of whether it will be positive or negative at neutral pH.

| | pKa 1 | pKa 2 | pKa 3 | pI | Presumed charge at pH 7 |
|---|---|---|---|---|---|
| Poly(L-lysine) | 2.18 | 8.95 | 10.53 | 9.74 | + |
| Polyethyleneimine | 8.04 | | | | + |

-continued

| | pKa 1 | pKa 2 | pKa 3 | pI | Presumed charge at pH 7 |
|---|---|---|---|---|---|
| Alanine | 2.34 | 9.69 | | 6.00 | − |
| Polyphosphoramidates | — | | | — | + |
| Polyphosphordiamidates | | | | | + |
| Protamine | 2.17 | 9.04 | 12.48 | 10.76 | + |
| Gelatine A | | | | 6-9 | + |
| Galatine B | | | | 5 | − |
| Chitosan | 6.5 | | | | |
| Polyamidoamine | 6.3 | 9.2 | | | + |
| Amine functional groups | 9-11 | | | | + |
| Dextrans | 5.5 | 9.2 | 14 | 8-9 | +/− |
| Cellulose derivatives | 6-13 | | | | + |
| Elastomers | | | | | − |
| Carboxylic functional groups | 4-5 | | | | − |
| Alginate | 3-4 | | | | − |
| Gum arabic | 2 | | | | − |
| Avidin (glycoprotein) | | | | 10.5 | + |

It will be understood that the surface treatment agent must be pharmaceutically acceptable since it is to be employed with drug nanoparticles.

Suitable surface treatment agents may be selected from one or more of poly(L-lysine), polyethyleneimine, alanine (amphoteric), polyphosphoramidates, protamine, gelatine (positive charge in acidic conditions), chitosan, polyamidoamine, poly(amino-co-ester)s, dextrans, celluloses and elastomers and from other sugars or small carboxylic acid functional groups and simple amine functional groups.

In embodiments the surface treatment agent is selected from one or more of poly(L-lysine), polyethyleneimine, polyphosphoramidates, protamine, and polyamidoamine. These agents are expected to be positively charged at neutral pH and may be useful for functionalising a negative carrier particle.

In embodiments the surface treatment agent is selected from one or more of alanine, chitosan, alginate and gum Arabic. These agents are expected to be negatively charged at neutral pH and may be useful for functionalising a positive carrier particle.

In embodiments the surface treatment agent comprises or consists of an organic group, such as one or more moieties selected from: alkyl, alkenyl, amine, carbonyl, ether, ester, sulphonyl, phenyl, cycloalkyl, cycloalkenyl and heterocycloalkyl moieties, each of which may optionally be substituted. The skilled reader will appreciate that one such moiety may by itself form the organic group, (for example, the organic group may be solely made up of an alkyl or cycloalkyl moiety), or that two or more such moieties may be combined to form the organic group (for example, the organic group may be made up of an alkyl moiety and a phenyl moiety, or a cycloalkyl moiety and an alkyl moiety). There may be two or more of the same type of moiety present within the organic group.

In embodiments the surface treatment agent is an organosilane such as an alkoxysilane or an aminosilane. Organosilanes are especially useful for functionalising silica and silicate carrier particles.

In embodiments the alkoxysilane is a monoalkoxysilane, a dialkoxysilane, a trialkoxysilane (e.g. 3-aminopropyl) trimethoxysilane, 3-mercaptopropyl)trimethoxysilane.

In embodiments the aminosilane is selected from primary aminosilanes, secondary aminosilanes, tertiary aminosilanes, and quaternary aminosilanes. In one embodiment the amino silane is bis[3-(trimethoxysilyl)propyl]amine.

In embodiments the carrier particle is MPS and the surface treatment agent is bis[3-(trimethoxysilyl)propyl] amine. In some embodiments, the drug nanoparticles could become trapped within the pores of the MPS pores. Hence, in some embodiments the carrier particle is not MPS. In further embodiments the carrier particle is not porous.

The surface treatment agent may have a low molecular weight. In embodiments the surface treatment agent has a molecular weight $M_w$ of 20 to 1000 g/mol or 50 to 500 g/mol. Such small molecules are especially useful for covalently bonding to the surface of the carrier particle.

In embodiments the surface treatment agent is a polymer, such as a naturally occurring polymer (biopolymer) or a synthetic polymer. Suitable naturally occurring polymers include proteins/polypeptides (e.g. protamine, gelatine) and polysaccharides (e.g. cellulose, dextran, chitosan, alginate, gum arabic, etc). Polymers are considered to be especially useful for adsorbing to the carrier particle surface.

In embodiments the surface treatment agent is protamine, a cationic polymer. Protamine has FDA approval as an inactive ingredient. Protamine can easily adsorb to clay following an ion-exchange process. Protamine has an isoelectric point of 10.76 and so it is positively charged at neutral pH while MMT is negatively charged.

In embodiments the carrier particle is MMT and the surface treatment agent is protamine.

In embodiments the surface treatment agent is a polymer that has a molecular weight ($M_w$) of no more than 20, 15, 10, 8 or 6 kDa and or at least 1, 3, 5 or 8 kDa. In embodiments the polymer has a molecular weight ($M_w$) of from 1 to 10 kDa or from 3 to 8 kDa. The molecular weight of the polymer should be selected to keep the drug nanoparticles as segregated as possible at maximum drug loading.

In one embodiment the surface treatment agent has a $M_w$ molecular weight of from 1 to 20 kDa.

In one embodiment the surface treatment agent has $M_w$ molecular weight of from 20 to 1000 g/mol.

In embodiments the surface treatment agent is a positively charged polymer (a cationic polymer) or negatively charged polymer (an anionic polymer).

Surface Functionalised Carrier Particle

The surface functionalised carrier particle has the surface treatment agent bonded thereto. In embodiments the surface treatment agent may be physically bonded to the carrier particle, e.g. protamine adsorbs to MMT clay. In embodiments the surface treatment agent may be chemically bonded to the carrier particle, e.g. organotrialkoxysilane covalently bonds to mesoporous silicate.

The amount of surface treatment agent per g of carrier material provides an indication of the surface coverage. In embodiments at least 1, at least 2, at least 3 or at least 5 mg surface treatment agent is bonded per g carrier particles and/or no more than 200, 100, 50 or 10 mg surface treatment agent is bonded per g carrier particles. In embodiments from 1 to 200 mg, from 2 to 100 or from 3 to 50 mg surface treatment agent is bonded per g carrier particles.

The surface treatment agent may be bonded to saturation level on the carrier particle. However, in some embodiments this will reduce the available adsorption sites for the drug nanoparticles. In embodiments the surface treatment agent is bonded below saturation level. The extent of functionalisation can be optimised to allow high drug loading and fast dissolution rates.

The amount of surface treatment agent that is bonded to the carrier particle can be determined by experiment. A suspension of the surface functionalised carrier particles can be analysed using a filter having openings smaller than the carrier particle and larger than the free surface treatment agent. The amount of free surface treatment agent that passes through the filter can be measured and then mass-balance can be used to determine the amount that is bonded.

The amount of surface treatment agent that is adsorbed to the carrier particle can be determined by experiment. For example, the carrier can be treated to release the surface treatment agent (e.g. by dilution in a solvent in which the agent is readily soluble) and the amount of surface treatment agent in solution is then measured (e.g. by UV-vis spectroscopy). Alternatively the carrier particles can be exposed to fixed amounts of surface treatment agent. The amount of adsorbed surface treatment agent is measured indirectly by measuring the amount of surface treatment agent that remains in solution after the functionalized carrier particles are removed by filtration.

In embodiments the surface functionalised carrier particle has a zeta potential of less than 50, 40, 30, 20, 10, 5 or 3 mV and/or at least −50, −40, −30, −20, −10, −5 or −3 mV.

In embodiments the surface functionalised carrier particle has a zeta potential of from −20 to 20 mV or from −10 to 10 mV. Close to neutral surface charge has been found to provide optimum dissolution behaviour. The protamine (PA) modified MMT exemplified in the present application has zeta potential of −6.1 mV at 4.6 mg PA/g MMT and 14.8 mV at 200 mg PA/g MMT. An example of a positively charged functionalised carrier particle is an amine functionalised silicate with a zeta potential in the range of +2 to 40 mV, depending on the level of amine functionalization. For example, it may be MPS functionalised with a (3-aminopropyl)triethoxysilane.

The ability of a particular functionalised carrier particle to stabilise drug nanoparticles will depend on a number of factors including the amount and properties of the surface treatment agent. In embodiments at least 3 mg surface treatment agent is bonded (e.g. adsorbed) per g carrier particle and the functionalised carrier particle has a zeta potential of from −15 mV to 15 mV or from −10 mV to 10 mV. In embodiments no more than 100 mg surface treatment agent is bonded (e.g. adsorbed) per g carrier particle and the functionalised carrier particle has a zeta potential of from −15 mV to 15 mV or from −10 mV to 10 mV.

Drug Nanoparticles

It will be understood that a drug nanoparticle is a nano particle of a drug i.e. a medicine or other substance which has a physiological effect when ingested or otherwise introduced into the body. A drug nanoparticle is a solid particle of drug molecules with a size dimension less than 1 μm; drug molecules are molecules which have a physiological effect when ingested or otherwise introduced into the body. According to the Biopharmaceutical Classification System (BCS) drug substances are classified to four classes based upon their solubility and permeability. The present invention is particularly useful for BCS Class II drugs, which have high permeability and low solubility. A drug substance is considered HIGHLY SOLUBLE when the highest dose strength is soluble in <250 ml water over a pH range of 1 to 7.5. A drug substance is considered HIGHLY PERMEABLE when the extent of absorption in humans is determined to be >90% of an administered dose, based on mass-balance or in comparison to an intravenous reference dose.

In embodiments the drug nanoparticles are nanoparticles of one or more of amiodarone, amprenavir, atorvastatin, carbamazepine, carvedilol, celecoxib, clofazimine, curcumin, cyclosporine, danazol, diclofenac, fenofibrate, glyburide, griseofulvin, ibuprofen, indinavir, indomethacin, itraconazole, ketoconazole, lovastatin, magestrol acetate, mefenamic acid, naproxen, nifedipine, ritonavir, saquinavir, simvastatin, sirolimus, spironolactone and warfarin.

In embodiments the drug nanoparticles are nanoparticles of one or more of amiodarone, amprenavir, atorvastatin, carbamazepine, carvedilol, celecoxib, clofazimine, curcumin, cyclosporine, danazol, diclofenac, fenofibrate, glyburide, griseofulvin, ibuprofen, indinavir, indomethacin, itraconazole, ketoconazole, lovastatin, magestrol acetate, mefenamic acid, naproxen, nifedipine, ritonavir, saquinavir, simvastatin, sirolimus, spironolactone, valsartan and warfarin.

In embodiments the drug is selected from the group comprising one or more of glibenclamide, bicalutamide, ezetimibe, phenytoin, aceclofenac, clofazimine, fenofibrate, and mefenamic acid, such as one or more of glibenclamide, bicalutamide, ezetimibe, phenytoin, aceclofenac, fenofibrate, and mefenamic acid. Each of these drugs is classified as BCS Class II.

In embodiments the drug is fenofibrate (FF).
In embodiments the drug is mefenamic acid (MEF).
In embodiments the drug is clofazimine.
In embodiments the drug is valsartan.

Nanoparticles are particles having an average diameter ($D_{50}$) less than 1 μm. In embodiments the drug nanoparticles have a $D_{50}$ value of at least 0.005, 0.01, 0.05, 0.1, 0.2, 0.3, 0.4, 0.5, 0.6 or 0.7 μm and/or no more than 0.95, 0.9, 0.85 or 0.8 μm. In one embodiment the drug nanoparticles have a $D_{50}$ value of from 0.7 to 0.8 μm.

In embodiments the drug nanoparticles have a zeta potential of less than zero, i.e. they are negatively charged. In embodiments drug nanoparticles have a zeta potential of less than −1, −3, −5, −7, −10, −15, −20, −25, −30 or −35 mV and/or at least −100, −80, −60, −40 −30 or −20 mV. The fenofibrate nanoparticles exemplified in the present application have a zeta potential of −25.3 mV.

In embodiments the drug nanoparticles have a zeta potential of greater than zero i.e. they are positively charged. In embodiments drug nanoparticles have a zeta potential of at least 1, 3, 5, 7, 10, 15, 20, 25, 30 or 35 mV and/or at no more than 100, 80, 60, 40, 30 or 20 mV.

In embodiments the carrier particle and/or the functionalised carrier particle has a negative zeta potential and the drug nanoparticles have either (i) a negative zeta potential or (ii) a positive zeta potential. The highest drug loading in the examples is achieved with a negative carrier particle (MMT), a positive surface treatment agent, a negative functionalised carrier particle (MMT-PA at 4.6 mg PA/g MMT) and a negative drug (fenofibrate). Hence, delicately balancing the zeta potential and surface charges has been shown to be successful.

In embodiments the carrier particle and/or the functionalised carrier has a positive zeta potential and the drug nanoparticles have either (i) a positive zeta potential or (ii) a negative zeta potential.

Composite

In embodiments the composite is provided in suspension, such as an aqueous suspension. The composite of the present invention has been found to be stable in suspension for 24 hours at standard ambient temperature and pressure (SATP, 25° C., 100 kPa).

In embodiments the composite is isolated in the solid state. In one such embodiment the composite is provided as a solid dosage form, such as a powder, a capsule containing a powder or a tablet.

In embodiments the composite comprises a clay carrier particle (e.g. MMT) having a surface that is functionalised with a polymer (e.g. protamine) and drug nanoparticles adsorbed thereto, wherein the drug nanoparticles comprise fenofibrate and/or mefenamic acid. Such composites demonstrate high drug loading and fast dissolution.

In embodiments the composite comprises an ethyl acrylate carrier particle having a surface that is functionalised with adipic acid dihydrazine and drug nanoparticles adsorbed thereto, wherein the drug nanoparticles comprise carbamazepine.

The drug loading in % w/w is the amount of drug in grams per 100 g of functionalised carrier particles. A high drug loading is beneficial for delivering a sufficient dose to a patient. In embodiments the composite has a drug loading of at least 2, 4, 6, 8, 9, 10, 15, 20, 30, 40 or 50% w/w. In embodiments the composite has a drug loading of no more than 100, 90, 80 or 70% w/w.

The capacity of the carrier for drug nanoparticles, i.e. the adsorption of drug nanoparticles to the carrier particles from suspension can be determined experimentally, for example, by centrifugation, dissolution testing or filtration. A sample of interest containing carrier particles having an unknown loading is compared to a sample containing drug nanoparticles only (no carrier) and a sample containing a carrier particles only (no drug nanoparticles, control).

The samples may be centrifuged (e.g. 5000 rpm for 2 minutes) and the supernatant decanted. The amount of drug in the supernatant is then measured (e.g. UV/vis spectroscopy) and used to estimate the amount that has sedimented i.e. amount of drug that has adsorbed to the carrier.

Alternatively the samples may be filtered using a filter having openings smaller than the carrier particles and larger than the free drug nanoparticles (e.g. 2.7 μm). The amount of drug in the filtrate is then measured (e.g. UV/vis spectroscopy) by dissolving a portion of the filtrate in a solvent (eg. methanol) and this value is used to determine the amount of drug that has bonded to the carrier.

The drug loading (% w/w) can also be determined by dissolution testing whereby a known mass of dry drug loaded carrier particles is dissolved in a known volume of dissolution media. The final concentration of the drug in the dissolution media is significantly below its saturation solubility. The concentration of drug in the dissolution media is measured by UV/Vis and/or HPLC spectroscopic methods until it stops increasing with time. The mass of drug present on the known mass of drug loaded carrier particles can thus be estimated and the drug loading in (% w/w) can be calculated.

According to a second aspect of the present invention there is provided a process for the preparation of the composite of the first aspect, the process comprising providing a suspension of drug nanoparticles in the presence of a carrier particle having an external surface, wherein the carrier particle surface is functionalised with a surface treatment agent.

The comments above in relation to the first aspect apply equally here and vice versa.

Typically, a plurality of carrier particles is used and a plurality of composites is thereby prepared.

In embodiments providing the suspension of drug particles comprises precipitating the drug nanoparticles from solution. For example, the drug may be dissolved in an organic solution and then precipitates on addition to an aqueous solution or water (i.e. anti-solvent precipitation), once a supersaturated solution is generated. Supersaturation can also be generated by cooling or solvent evaporation.

In embodiments providing the suspension of drug nanoparticles comprises comminuting a drug to reduce its particle size and thereby provide drug nanoparticles.

In embodiments the solution (or saturated solution) and/or suspension consists of the solvent (e.g. water, or organic solvent or water/organic solvent mixture), the drug and the surface functionalised carrier particles, i.e. no further stabilisers are present. Khan et al employed drug-specific soluble stabilisers but the process of the present invention can be carried out without additional stabilisers.

In embodiments providing a suspension of drug nanoparticles comprises precipitating drug nanoparticles from solution in the presence of carrier particles.

In embodiments providing a suspension of drug nanoparticles comprises precipitating drug nanoparticles from solution and combining with a carrier particle after precipitation. The drug suspension can be added to a suspension (e.g. an aqueous suspension) of carrier particles or the suspension of carrier particles can be added to the drug suspension. The inventors have determined that the composite will form even if the carrier particles are added after precipitation. It will be understood that a suspension of drug nanoparticles is unstable and therefore the carrier particles should be added as soon after precipitation as is practical. In one such embodiment the carrier particle is added no later than 60, 30, 15 or 5 minutes after precipitation. In embodiments the carrier particle is added no later than 90, 60 or 30 seconds after precipitation.

It will be appreciated that the liquid medium used in the suspension of carrier particles is chosen to be a liquid (a) that is pharmaceutically acceptable and (b) in which the carrier particles are insoluble. As discussed above in relation to the carrier particles, in embodiments the carrier particles are water-insoluble, and in embodiments the carrier particles are insoluble in organic solvent e.g. ethanol.

In embodiments the process additionally comprises an initial step of functionalising the surface of the carrier particle with a surface treatment agent (before providing the suspension of drug nanoparticles). In one such embodiment a solution of the surface treatment agent is provided and the carrier particles are combined with the solution e.g. added to the solution.

In embodiments the process additionally comprises isolating the resulting composite(s) from suspension. The composites of the present invention can be isolated from suspension more easily that the corresponding "free" drug nanoparticles.

In embodiments the composites are isolated by filtration. In embodiments the composites are isolated by filtration of the suspension through a filter (e.g. a mesh, sieve, filter paper) having openings, wherein the openings have a size of at least 0.5, 1, 1.5, 2, 5 10 or 25 μm and/or no more than 500, 300, 100, 50, 25, 20, 10 or 15 μm.

In embodiments the composites are isolated by centrifugation. Centrifugation can be carried out more easily for the composites of the invention than on the corresponding "free" drug nanoparticles.

In embodiments the process additionally comprises drying the isolated composites. In one such embodiments the isolated composites are dried under vacuum, e.g. at a reduced pressure of less than 50 kPa or less than 30 kPa.

In embodiments the process additionally comprises formulating the isolated composite into a solid dosage form. For example, the solid composite can be tabletted or placed in capsules.

According to a third aspect of the present invention there is provided the composite of the first aspect for use as a medicament.

The present invention will be further described by reference to the following figures and non-limiting examples in which.

Figure 1:
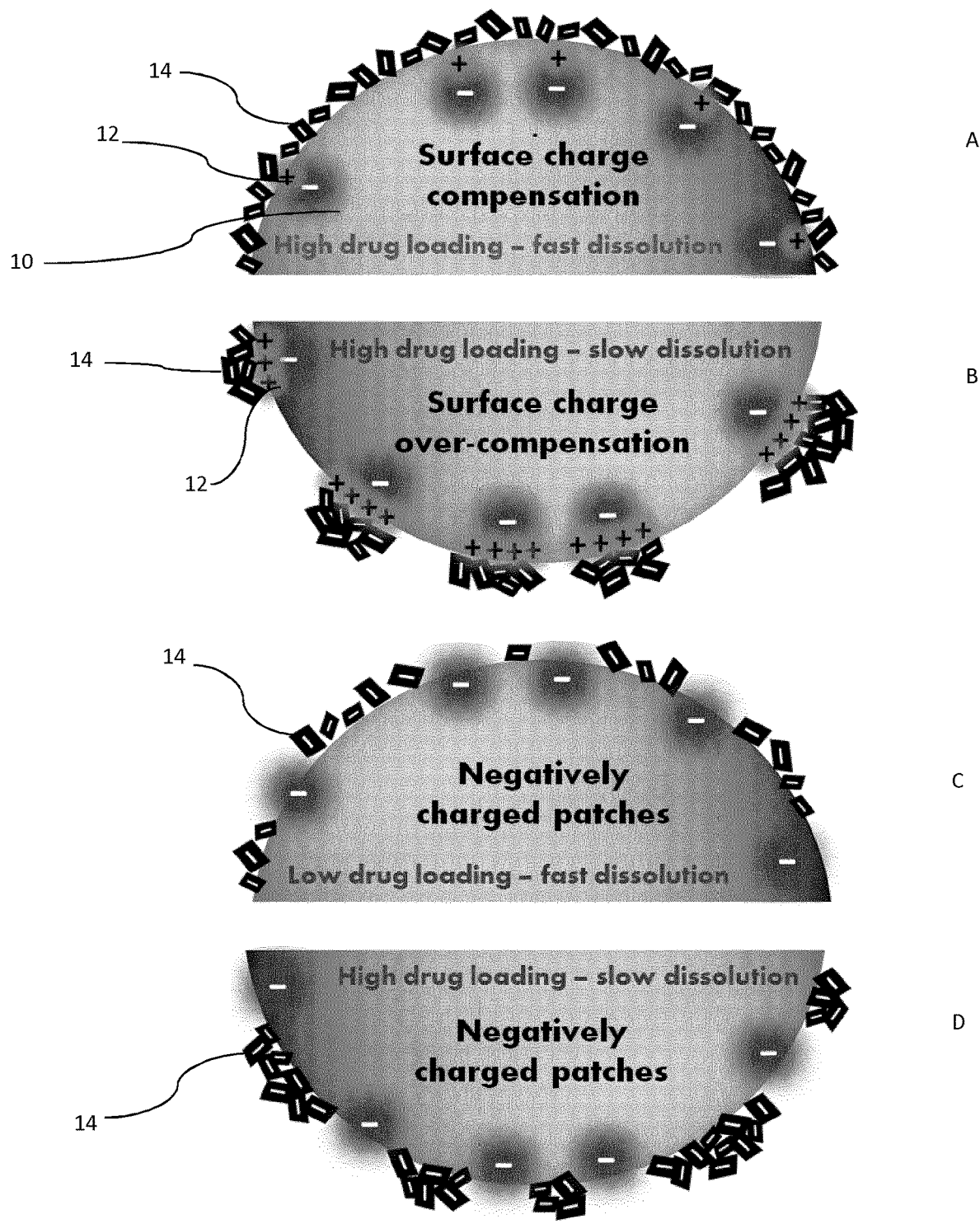
FIG. 1 is a schematic diagram illustrating a possible mechanism for embodiments of the present invention.
Figure 2:
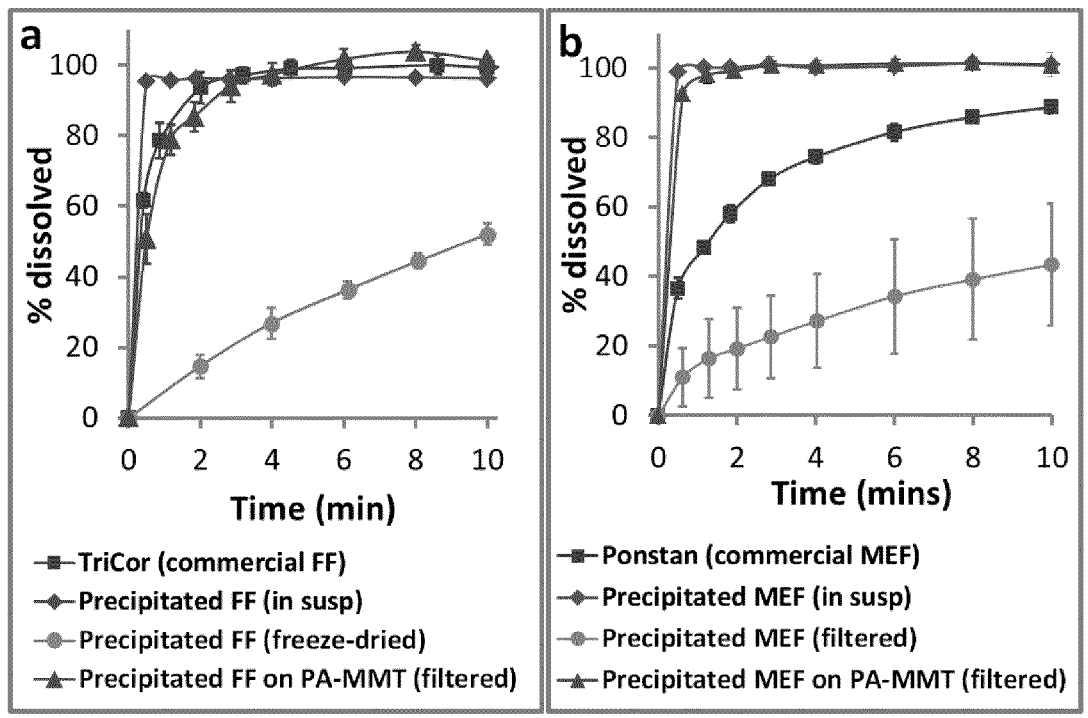
FIG. 2 shows dissolution profiles of (a) fenofibrate (in 0.1M HCl with 0.4% w/v Tween-80 at 42° C.) and (b) mefenamic acid (in 0.05M pH 7.4 phosphate buffer at 37° C.), comparing commercial formulations, and precipitated material in suspension and after drying (1 min aging time)

Without being bound by theory the inventors propose that a mechanism may be described with reference to FIGS. 1A to 1D. Each of FIGS. 1A and 1B shows a negatively charged carrier particle 10 which is surface functionalised with a positively charged surface treatment agent 12 to adsorb negatively-charged, hydrophobic drug nanoparticles 14. In FIG. 1A the positive surface treatment agent 12 compensates the negative charge of the carrier particle 10 thereby increasing the availability of favourable adsorption sites to provide a uniform and segregated dispersion of drug nanoparticles 14. This provides high drug loading and fast dissolution in vivo. In FIG. 1B, a greater amount of surface treatment agent 12 is employed, such that the negative charge of the carrier particle 10 is overcompensated. The nanoparticles 14 preferentially bind to the positive sites through electrostatic forces. Although a high drug loading is achieved, the drug particles 14 are slow to dissolve.

FIGS. 1C and 1D show the same carrier particle 10, without surface functionalisation. In the absence of surface functionality, negatively-charged, hydrophobic drug nanoparticles bind to the hydrophobic patches of the carrier particle surface through hydrophobic interactions, but will strictly avoid the negatively charged regions due to electrostatic repulsion. At low drug loadings (FIG. 1C), the hydrophobic surface area of the carrier is sufficient to bind dispersed drug nanoparticles which maintain their high surface area (and resulting fast dissolution rates) when bound to the carrier. However, the hydrophobic surface area of the carrier particle is limited. On increasing the drug loading (FIG. 1D), nanoparticles aggregate at the hydrophobic sites. This results in a loss of nanoparticle-induced high surface area and a consequential reduction in dissolution rate.

Hence, a high drug loading and high rate of dissolution can be obtained by balancing the charges on the carrier particle with an appropriate amount of surface treatment agent. Although the mechanism has been illustrated with respect to a negative carrier particle and a positive surface treatment agent, the mechanism is also applicable to a positive carrier particle and negative surface treatment agent.

Methodology

Materials

Fenofibrate (as received, 99.7% purity) and fenofibrate choline salt (crude) were generously gifted from Abbvie Laboratories. Converted fenofibrate (FF) was prepared from the salt form as explained below. Ethanol (99.8%) was purchased from Merck Millipore. Mefenamic acid (MEF, Form I, >98%), N, N-dimethylacetamide (DMA, >99.9%), montmorillonite K10 (MMT), protamine sulphate salt from salmon (PA, amorphous, approx. 5.1 kDa), hydrochloric acid, Tween-80, isopropanol (≥99.9%), thionyl chloride (≥99.9%) and potassium carbonate (≥99%) were purchased from Sigma Aldrich. Potassium dihydrogen phosphate and disodium hydrogen phosphate were purchased from VWR International. TriCor tablets (commercial nanoformulation of FF) were purchased from Abbott. Ponstan capsules (commercial micron formulation of MEF) were purchased from Chemidex Pharma Ltd. Distilled water was used for sample preparations.

Conversion of Fenofibrate Choline Salt to Fenofibrate

Fenofibrate was prepared from fenofibrate choline salt by the literature method (US20100185008).

Functionalisation of the Montmorillonite Surface

Protamine sulphate salt was dissolved in 10 mL water at concentrations ranging from 0.05-10 mg/mL. Montmorillonite clay (0.4 g-1 g) was added to the protamine solution, and agitated at 25° C. for >2 hrs. The surface coverage of protamine on montmorillonite was altered by increasing the ratio of protamine to MMT (2-1000 mg PA/g MMT) until the saturation limit of the MMT surface was reached. PA-MMT samples were equilibrated for >2 hrs, before vacuum-filtering using Whatman filter paper 50 (2.7 μm pore, 35 mm cross-section). The concentration of protamine lost to the filtrate was measured by UV-vis spectroscopy (Shimadzu UV-1280) at a wavelength of 200 nm and served as an indication of the protamine attachment to the MMT.

Zetapotential Determination

Zetapotential measurements were conducted on a Malvern Zetasizer Nano ZSP system. Zetapotential was determined from the electrophoretic mobility using the Smoluchowski approximation. The samples (without dilution) were filled into a folded capillary cell and equilibrated at 25° C. for 120 s before measurement. Three measurements were taken per run and each sample was run twice. The average value and the variation between measurements were reported.

Synthesis of Nanoparticles and their Loading onto Carrier Particles

Nanoparticles of both fenofibrate (FF) and mefenamic acid (MEF) were generated by antisolvent precipitation. An organic solution of FF in ethanol (1 mL, 50 mg/mL) was quickly introduced by Eppendorf pipet to 10 mL antisolvent containing (a) water, (b) an MMT suspension in water (50 mg/mL, equilibrated for >2 hrs) or (c) a protamine-modified MMT suspension in water (50 mg/mL, 4.6-189.9 mg PA/g MMT, equilibrated for >2 hrs). Solutions/suspensions were maintained at 25° C. under rapid agitation (800 rpm) throughout the precipitation process. For standard experiments, particles were aged for 1 min before drying. Exceptions were made for stability testing. Aging time refers to the time period from precipitation to isolation during which the particles are held in suspension. Two additional experiments were conducted at (i) 100 mL scale and (ii) where the protamine-modified MMT suspension (50 mg/mL, 4.6 mg PA/g MMT, equilibrated for >2 hrs) was added to the water-precipitated fenofibrate suspension at 20 s after precipitation, and aged for an additional 1 min before drying. FF nanoparticles from preparation (a) were isolated by freeze-drying on a Dura-Dry Microprocessor Control freeze-dryer at <20 Pa for 48 hrs after flash-freezing in liquid nitrogen. Particles from all other preparations were isolated by vacuum-filtration (Mini diaphragm vacuum pump, VP 86) using Whatman filter paper 50 (2.7 μm pore, 35 mm cross section), and washed with 2 mL water. Filter cakes were dried under vacuum (<20 Pa) for 24 hrs.

Attachment of FF nanoparticles to the carrier was indirectly monitored by measuring the FF content lost to the filtrate (through the 2.7 μm filter pore) using a Shimadzu UV-1280 UV-vis spectrophotomer ($\lambda$=289 nm). Unattached nanoparticles could pass through the filter to produce a milky filtrate, while carrier-attached nanoparticles could not, resulting in a clear filtrate. An aliquot of the filtrate was diluted by a factor of 10 in methanol and equilibrated for 24 hrs to dissolve any FF present before measuring the dissolved concentration.

Centrifugation was further used to distinguish whether the FF nanoparticles adsorbed to the PA-modified MMT or if the MMT simply served as a filtration aid to remove the FF nanoparticles from suspension. Samples containing free FF nanoparticles, a PA-MMT control, and a FF-PA-MMT composite were aged for 0.5 min before centrifuging at a speed of 5000 rpm for 2 min. The supernatant was decanted into a separate vial and the FF content in the supernatant was measured by UV/vis spectroscopy after dissolving a portion in methanol and leaving to equilibrate for 24 hrs. On knowing the FF content in the supernatant, a mass balance was used to estimate the % of FF which sedimented. This was used as an indicator of the % of FF which adsorbed to the PA-MMT carrier from suspension.

Suspended nanoparticles of MEF were prepared and isolated as follows. An organic solution of MEF in DMA (0.5 mL, 40 mg/mL, 25° C.) was quickly introduced by Eppendorf pipet to a 9.5 mL aqueous solution of docusate sodium salt (0.53 mg/mL, 5° C.) antisolvent under rapid agitation (1200 rpm). After 1 min aging, free nanoparticles were isolated from suspension by filtration with a nylon membrane (0.2 μm). To prepare nanoparticle-carrier composites, MEF was precipitated under the same conditions but with the replacement of the docusate sodium stabiliser in the antisolvent for protamine-modified MMT (42 mg/mL MMT in water, 4.6 mg PA/g MMT). After 1 min aging, particles were vacuum filtered in the same way as the fenofibrate-carrier composites.

Dissolution Testing

The dissolution medium for FF samples consisted of a 0.1 M HCl solution containing 0.4% w/v Tween 80 at 42° C. The dissolution medium for MEF samples consisted of a 0.05 M pH 7.4 phosphate buffer with 0.05% w/v Tween-80 at 37° C. Dissolution tests were carried out in sink conditions by adding a sample (powder or suspension) containing 12.5 mg API to 450 mL dissolution medium under agitation of 400 rpm. TriCor tablets (commercial FF) were ground to a powder by pestle and mortar for 2 min prior to dissolution testing. The powder contained in Ponstan capsules (commercial MEF) was extracted from the capsules for use in dissolution testing. After sample addition, 4 mL aliquots were taken at regular intervals from the bulk solution in preheated (45° C.) plastic syringes and filtered through preheated (45° C.) PTFE 0.2 μm syringe filters. The dissolved drug concentration of both FF and MEF was measured by UV/visible spectroscopy (Shimadzu UV-1280) at a wavelength of 289 nm. Dissolution tests were carried out at least in duplicate. Results are shown in FIGS. 2, 6, 7 and 10.

Particle Size Analysis

Figure 3:
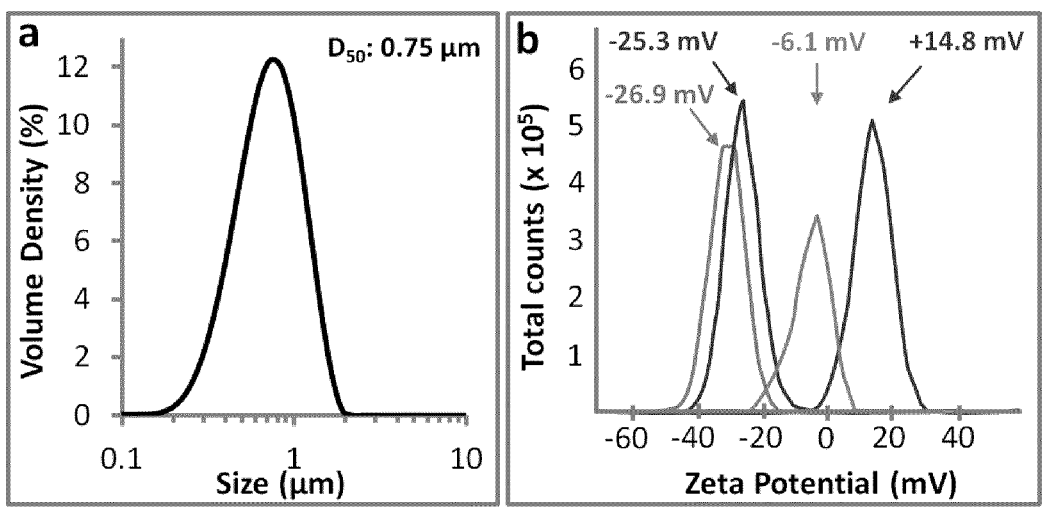
FIG. 3 shows (a) particle size distribution of precipitated fenofibrate (no carrier, 1 min aging time) and (b) zeta potential distributions for precipitated fenofibrate nanoparticles (−25.3 mV), MMT carrier (−26.9 mV) and PA-modified MMT (−6.1 mV at 4.6 mg PA/g MMT, +14.8 mV at 200 mg PA/g MMT)
Figure 4:
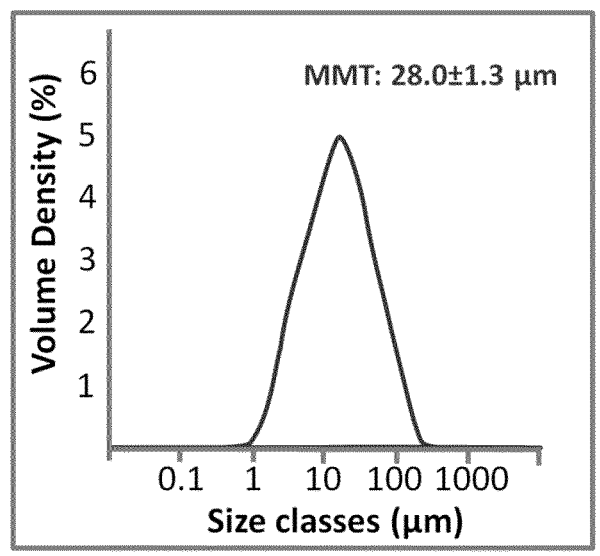
FIG. 4 shows the particle size distribution of montmorillonite clay employed in the examples.

Particle size measurements were performed by laser diffraction using a Malvern Mastersizer 3000, with water as the dispersion medium. In cases where the particle size was not stable, HPMC and SDS were added to the water dispersant at a concentration of 0.038 mg/mL each to minimise variation between consecutive measurements. Precipitated drug suspensions were diluted by a factor of 5 with water prior to their introduction to the measurement vessel. An MMT control was treated by the conditions used during antisolvent precipitation before measuring its particles size. An obscuration rate of 7-10%, a stir rate of 2300 rpm, a 1 min pre-measurement delay (including 20 sec with 5% sonication power) were the conditions used during all size measurements. A refractive index of 1.55 and an absorption index of 0.01 were used for FF measurements. A refractive index of 1.55 and an absorption index of 0.1 were used for MMT measurements. Four measurements were taken per run and each sample was run twice. The $D_{50}$ was reported for each size distribution and averaged across all measurements. Measurement variations were also reported. Results are shown in FIGS. 3 and 4.

X-Ray Powder Diffraction

X-ray diffraction patterns of the powders were recorded using a PANalytical Empyrean diffractometer in transmission mode, using Ni filtered CuKα radiation ($\lambda$=1.54 Å) at 40 kV and 40 mA. The XRD data was recorded in the range of 20.5-23.0° 2θ for FF samples and the range 14.5-16.5° 2θ for MEF.

Discussion

Nanosizing has been shown to improve the dissolution properties of both FF and MEF. Stabilised nanosuspensions of FF (T. B. Tierney, Y. Guo, S. Beloshapkin, Å. C. Rasmuson and S. P. Hudson, Cryst. Growth Des., 2015, 15, 5213-5222) and MEF (not yet published) were prepared by antisolvent precipitation in the presence of dissolved polymer and surfactant-based additives. However, in both cases, the dissolved additives were incapable of stabilising the nanoparticles during isolation and drying, causing them to forego their nanoparticle-induced dissolution enhancement. In the present invention, the nanoparticles were captured from suspension and stabilised on the surface of a clay carrier excipient. Carrier-bound nanoparticles were isolated from suspension by filtration, and their fast nanoparticle-induced dissolution rates were preserved during the isolation and drying process, FIG. 2. The previously used optimum additives for each drug system were omitted in the presence of clay particles, as their function was made redundant.

The carrier, montmorillonite (MMT), a negatively charged (FIG. 3*b*) aluminosilicate clay with high ion-exchange capacity, average size: 28 μm, (FIG. 4) and its surface modification agent (protamine, PA) have FDA approval as inactive ingredients. Protamine, a cationic polymer, can easily adsorb to the clay following an ion-exchange process and attract negatively charged drug nanoparticles to the carrier surface.

Figure 5:
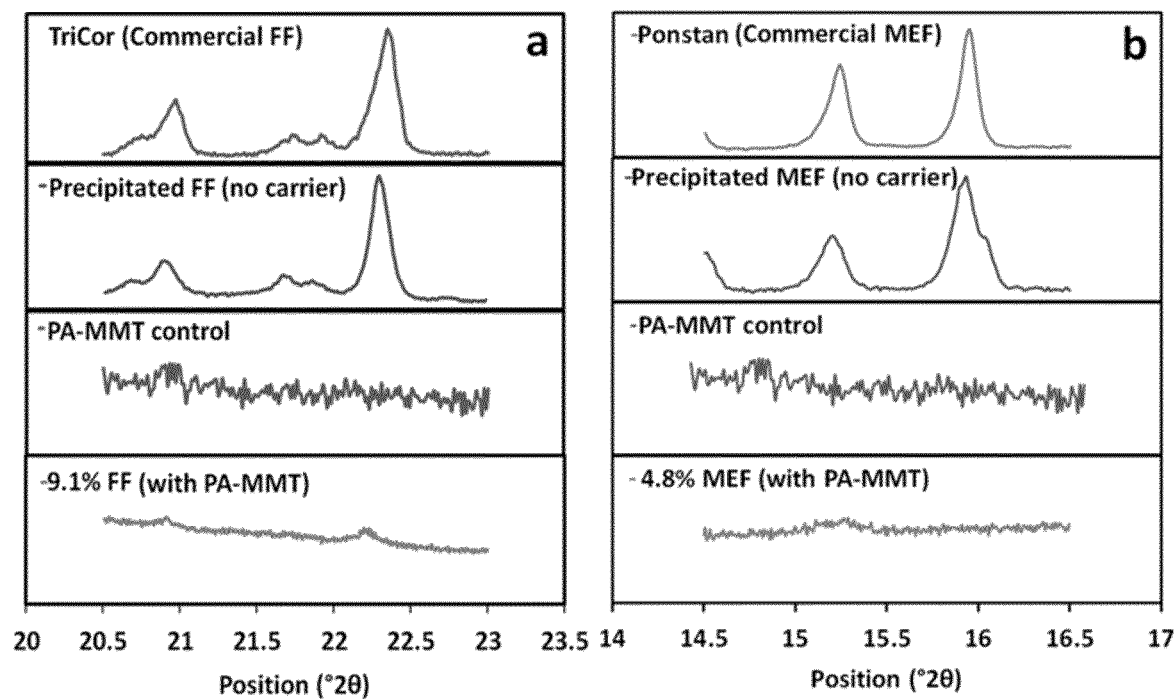
FIG. 5 shows X-ray diffraction patterns for (a) fenofibrate and (b) mefenamic acid, comparing commercial formulations and precipitated material after drying (1 min aging time)
Figure 6:
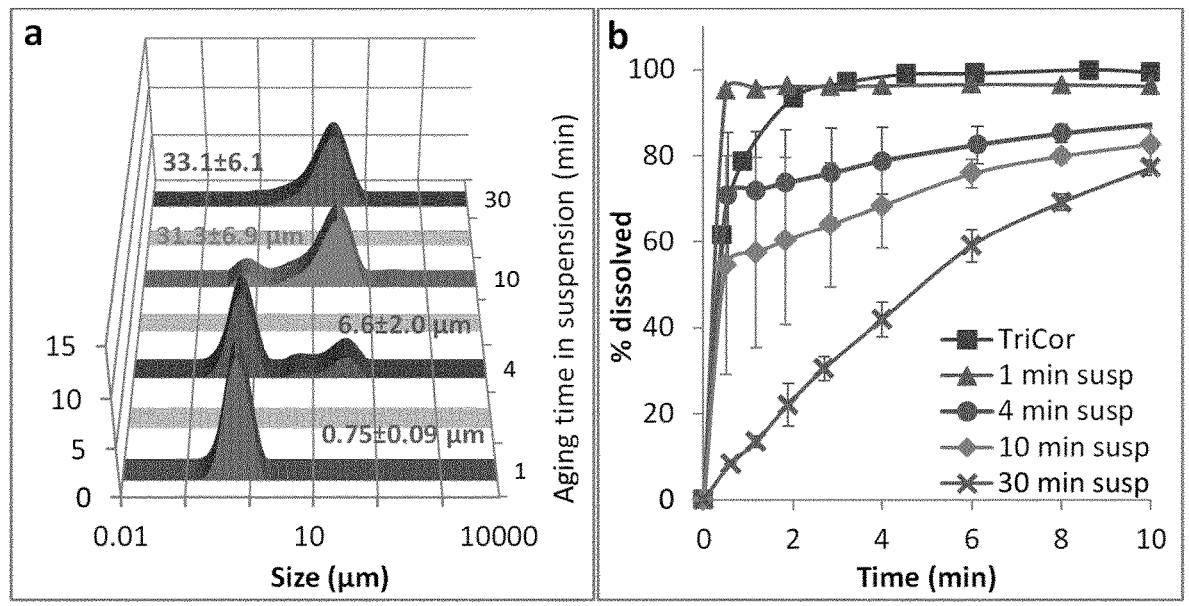
FIG. 6 shows (a) evolution of the particle size distributions over time for FF precipitated in water with no stabilising additives, including the average particle size from each distribution, and (b) their corresponding dissolution profiles.
Figure 7:
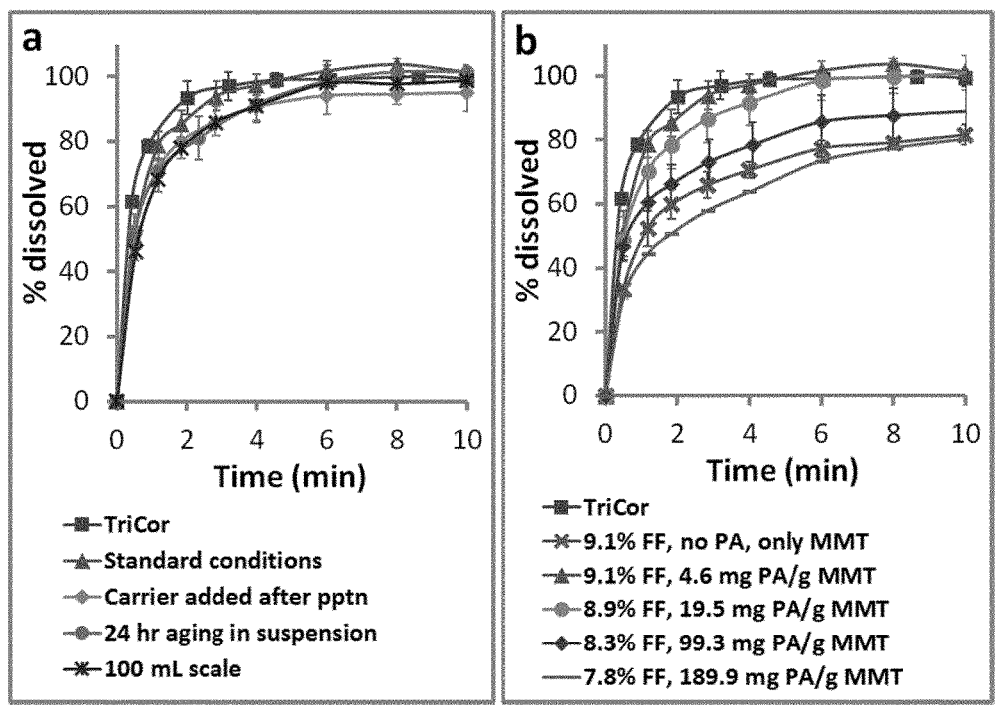
FIG. 7 shows dissolution profiles highlighting (a) the influence of variation from standard conditions (i.e. carrier present during precipitation, 1 min aging, 10 mL scale) and (b) the influence of PA coating density on MMT carrier (in 0.1M HCl dissolution medium with 0.4% w/v Tween-80 at 42° C.)

Particle sizing showed that, although highly unstable, nanoparticles of fenofibrate ($D_{50}$: 0.75±0.09 μm, ZP: −25.3 mV FIG. 2) and mefenamic acid ($D_{50}$: 0.84±0.05 μm, ZP: −35.3 mV) could be prepared in suspension by antisolvent precipitation in pure water, with both nanoparticle systems possessing a negative zeta potential. These suspended nanoparticles, without carrier, were crystalline (confirmed by XRD, FIG. 5) and dissolved rapidly in the dissolution medium, FIG. 2. However, without the protection of the dissolved stabilisers, the particle size quickly increased over time when held in suspension. Consequentially, the dissolution rates decreased with aging time (shown for fenofibrate system in FIG. 6). In such cases immediate nanoparticle isolation is necessary to prevent dissolution rate reduction by particle enlargement.

MMT clay was sparsely surface-functionalised with PA prior to loading with the drug nanoparticles. Addition of the functionalised clay to the nanosuspension either before (standard conditions) or 20 s after precipitation resulted in immediate adsorption of the drug nanoparticles to the carrier surface, allowing >99.5% drug recovery from the suspension when filtered with a 2.7 μm filter (compared to <20% recovery with no carrier). Centrifugation further confirmed nanoparticle adsorption to the carrier, since carrier-attached nanoparticles underwent almost complete sedimentation during centrifugation (98%) while free nanoparticles did not (30% sedimentation). Crystallinity of drug nanoparticles appeared to be maintained when loaded onto the PA-MMT carrier based on XRD analysis (FIG. 5, albeit low intensity peaks), and further based on the similarity in dissolution profiles when the carrier was added to the suspension of crystalline nanoparticles either before or shortly after precipitation, FIG. 7a. Carrier-bound nanoparticles were stable in suspension up to 24 hours after precipitation, as indicated by an unchanging dissolution profile over time (FIG. 7a). This therefore indicates preservation of the large surface area of the nanoparticles with time in the liquid state, and introduces flexibility to their isolation timeline so that immediate drying (i.e. by freeze-drying) is not required.

Following a rapid filtration step (<0.5 min), the drug-loaded composites were vacuum-dried over-night at <27 Pa. Upon redispersion, the dissolution profile of the solid-state material was comparable to that of the original suspended nanoparticles, FIG. 2. Furthermore, dissolution profiles of the solid nanocomposites matched that of the commercial nanoformulation of fenofibrate (TriCor prepared by milling) and surpassed that of the commercial micron formulation of mefenamic acid (Ponstan). The drug loadings on the PA-MMT carrier, 9.1% for fenofibrate and 4.8% for mefenamic acid, fall within the typical ranges used in excipient formulations in industry. The process was scalable (at least ×10) from its original 10 mL antisolvent scale, without significant influence on the dissolution behaviour (FIG. 7a). Surface-modification of the negatively-charged clay with positively-charged PA was necessary to obtain a homogeneous dispersion of negatively-charged nanoparticles on the clay surface by increasing the availability of favourable adsorption sites (see FIG. 1). Protamine interacts with the clay surface through electrostatic forces following a cation-exchange process, providing it with a positively-charged polymeric coating. However, the surface coverage of PA on the MMT was influential in obtaining a uniform and segregated dispersion of the nanoparticles on the clay surface, by balancing positive and negative charges.

Figure 8:
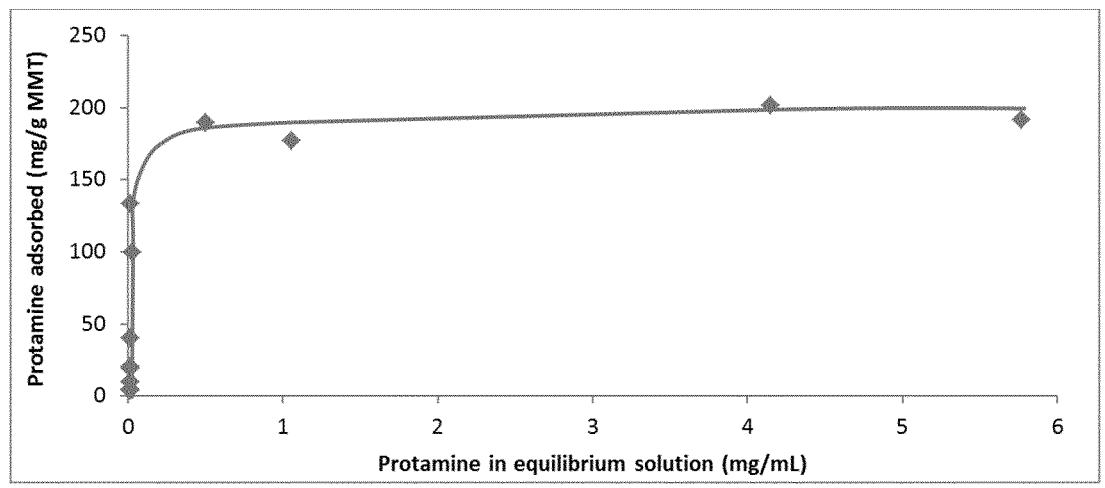
FIG. 8 shows the adsorption isotherm for PA onto MMT.
Figure 9:
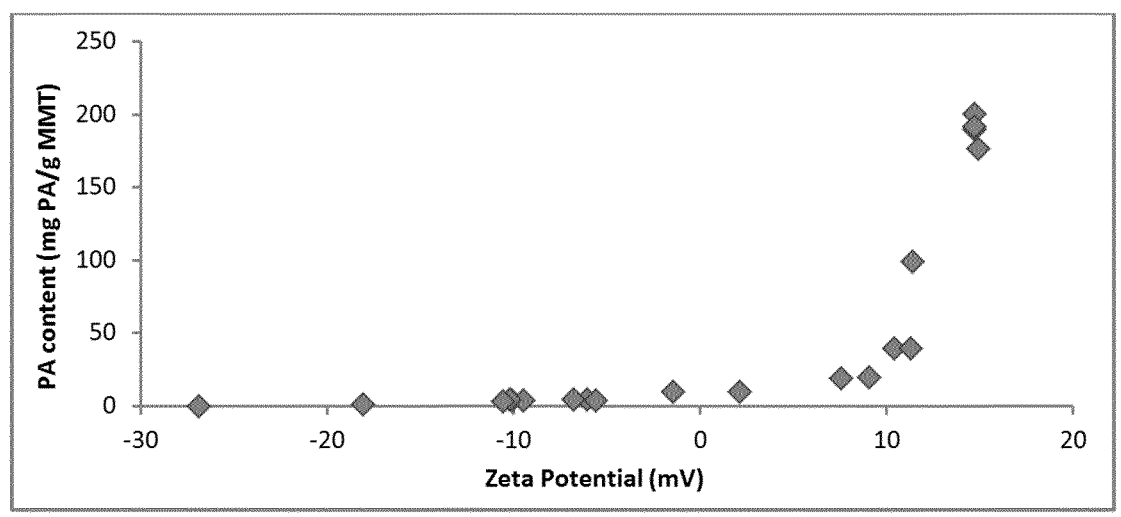
FIG. 9 shows surface charge (zeta potential, ZP) modification of MMT with PA.
Figure 10:
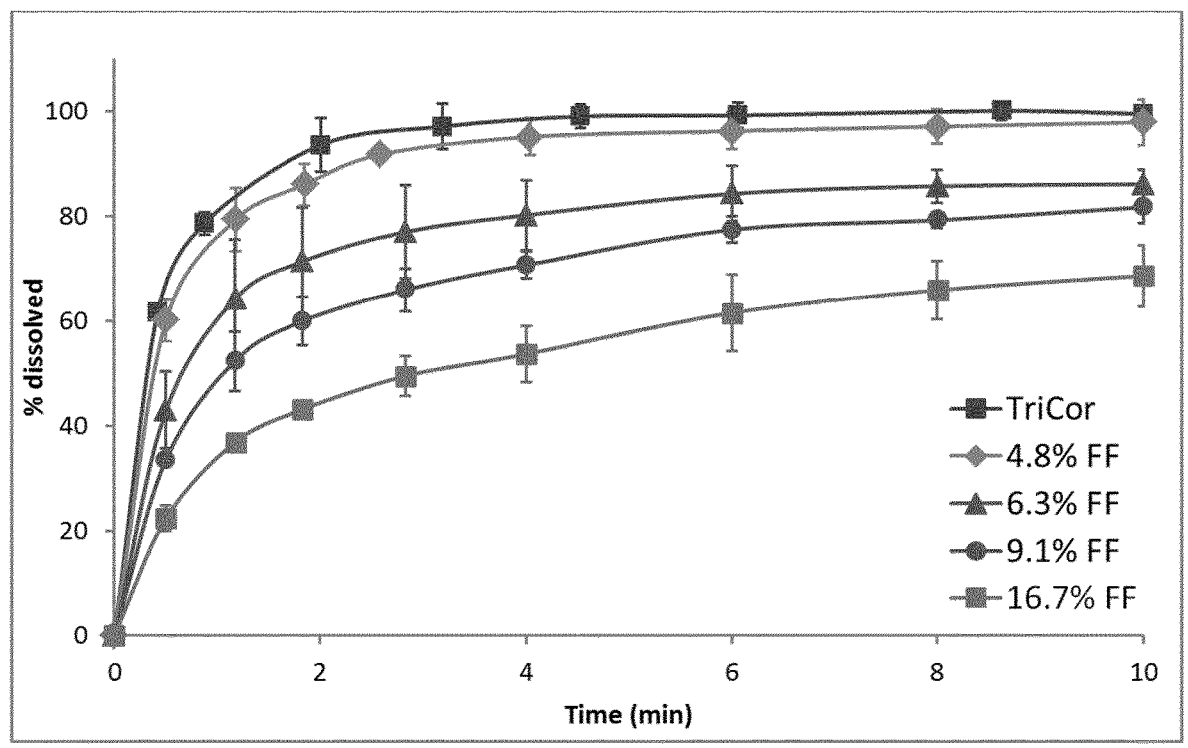
FIG. 10 shows the dissolution rate of FF from FF-MMT composites at various drug loadings (no PA content).

The zeta potential of MMT was modified from negative (−26.9 mV) to positive (14.8 mV) by the adsorption of PA to saturation level (200 mg PA/g MMT), FIG. 3b (also FIGS. 8 and 9). However, increasing the surface coverage of PA on MMT towards the saturation limit reduced the dissolution rate of the carrier-bound nanoparticles, FIG. 7b. Sparse PA coverage (4.6 mg PA/g MMT) and close to neutral surface charge (approx. −6 mV, FIG. 9) were the conditions required for optimum (fastest) dissolution behaviour. Control tests in the absence of PA but at equal drug loading (9.1%) showed that nanoparticles fully adsorbed to the unmodified clay (>99.5%). However, the dissolution rate of FF particles from the unmodified carrier was lower than that of particles from a sparsely PA-modified carrier, FIG. 7b. Lowering the drug loading on the unmodified clay to 4.8% improved the dissolution rate (FIG. 10) due to a higher available surface area for segregated adsorption of nanoparticles (see FIG. 1). However, reducing the drug loading was an undesirable route to achieve rapid dissolution. Sparse modification of the clay surface with PA facilitated rapid dissolution at the higher drug loading (9.1%), FIG. 7b.

CONCLUSION

Negatively charged nanoparticles generated in suspensions from a supersaturated solution during an antisolvent precipitation method were isolated with a cationic polymeric functionalised microparticle carrier system. This nanoparticle composite (with up to 9% w/w drug loading) was stable in suspension for 24 hours at SATP and could be filtered quickly to produce a solid nanoparticle composite that exhibited enhanced dissolution rates, attributed to the increased surface area of the nanoparticles. Without the carrier, filtration was difficult and the dissolution rate was slow. Without the cationic polymer functionalisation on the carrier, filtration was possible but the dissolution rate was still slow. Thus the combination of a microparticle carrier to improve filtration times and an optimal level of cationic polymer, preserved the enhanced dissolution rate of the nanoparticle suspension created from the supersaturated solution and allowed for isolation by filtration.

The process described here was validated with two drugs, but has generic potential in the preparation and isolation of all negatively-charged drug nanoparticles. Furthermore, the same rationale may be applied to other combinations of carriers and charged surface treatment agents for tailored application to any drug molecule, giving this system significant applicability for the formulation of solid-state drugs, especially, BCS Class II drugs.

The invention claimed is:

1. An isolated composite comprising a carrier particle and a plurality of drug nanoparticles, wherein the carrier particle has an external surface that is functionalised with a surface treatment agent and the plurality of drug nanoparticles is adsorbed onto the functionalised external surface.

2. The composite of claim 1, wherein the carrier particle has a $D_{50}$ particle size of from 1 to 500 μm.

3. The composite of claim 1, wherein the carrier particle is an inorganic carrier particle.

4. The composite of claim 3, wherein the carrier particle is a clay carrier particle.

5. The composite of claim 1, wherein the carrier particle is an organic carrier particle.

6. The composite of claim 1, wherein the surface treatment agent is a polymer.

7. The composite of claim 1, comprising from 1 to 300 mg surface treatment agent per gram carrier particle.

8. The composite of claim 1, wherein the drug nanoparticles have a $D_{50}$ value of less than 0.95 μm.

9. The composite of claim 1, wherein the drug nanoparticles have a negative zeta potential at neutral pH.

10. The composite of claim 1, wherein the carrier particle that is functionalised with the surface treatment agent has a negative zeta potential.

11. A process for the preparation of an isolated composite comprising a carrier particle and a plurality of drug nanoparticles, the process comprising providing a suspension of drug nanoparticles in the presence of a carrier particle, the carrier particle having an external surface that is functionalised with a surface treatment agent and the plurality of drug nanoparticles being adsorbed onto the functionalised external surface.

12. The process of claim 11, wherein providing the suspension of drug nanoparticles comprises precipitating the drug nanoparticles from solution.

13. The process of claim 11, wherein providing the suspension of drug nanoparticles comprises comminuting a drug to prepare drug nanoparticles.

14. The process of claim 11, additionally comprising an initial step of functionalising the surface of the carrier particle with a surface treatment agent.

15. The process of claim 14, wherein the carrier particle has a zeta potential and functionalising the surface of the carrier particle with the surface treatment agent comprises a reduction in the magnitude of the zeta potential.

16. The process of claim 11, additionally comprising isolating the composite from suspension.

17. The process of claim 16, wherein the composite is isolated by filtration.

18. The process of claim 16, additionally comprising drying the isolated composite.

19. The process of claim 16, additionally comprising formulating the isolated composite into a solid dosage form.

* * * * *